United States Patent
Miller et al.

(10) Patent No.: US 11,723,515 B2
(45) Date of Patent: Aug. 15, 2023

(54) SURGICAL TOOL HAVING INTEGRATED MICROPHONES

(71) Applicant: Verb Surgical Inc., Santa Clara, CA (US)

(72) Inventors: Denise Ann Miller, Scotts Valley, CA (US); Joan Savall, Palo Alto, CA (US); Geoffrey Robert Russell, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 38 days.

(21) Appl. No.: 17/217,992

(22) Filed: Mar. 30, 2021

(65) Prior Publication Data

US 2021/0287649 A1 Sep. 16, 2021

Related U.S. Application Data

(60) Continuation of application No. 16/734,227, filed on Jan. 3, 2020, now Pat. No. 10,991,357, which is a
(Continued)

(51) Int. Cl.
*A61B 34/30* (2016.01)
*H04R 3/00* (2006.01)
(Continued)

(52) U.S. Cl.
CPC ........ *A61B 1/00042* (2022.02); *A61B 1/0004* (2022.02); *A61B 1/04* (2013.01);
(Continued)

(58) Field of Classification Search
CPC ... H04R 1/00; H04R 1/02; H04R 1/04; H04R 1/08; H04R 1/028; H04R 1/1083;
(Continued)

(56) References Cited

U.S. PATENT DOCUMENTS 5,033,082 A 7/1991 Eriksson et al.
6,925,357 B2 8/2005 Wang et al.
(Continued)

FOREIGN PATENT DOCUMENTS

DE 10333488 A1 2/2005
EP 1929933 A2 6/2008
(Continued)

OTHER PUBLICATIONS

International Search Report and Written Opinion dated May 20, 2019 for related PCT Appln. No. PCT/US2018/048801 21 Pages.
(Continued)

*Primary Examiner* — Thang V Tran
(74) *Attorney, Agent, or Firm* — Aikin & Gallant, LLP

(57) ABSTRACT

Communication apparatus and devices for surgical robotic systems are described. The communication apparatus can include a user console in communication with a communication device having a surgical tool. The communication device can include a microphone to convert a sound input into an acoustic input signal. The communication device can transmit the acoustic input signal to the user console for reproduction as a sound output for a remote operator. The surgical tool can include an endoscope having several microphones mounted on a housing. The surgical tool can be a sterile barrier having a microphone and a drape. The microphone(s) of the surgical tools can face a surrounding environment such that a tableside staff is a source of the sound input that causes the sound output, and a surgeon and the tableside staff can communicate in a noisy environment. Other embodiments are also described and claimed.

20 Claims, 7 Drawing Sheets

Related U.S. Application Data division of application No. 15/999,676, filed on Aug. 20, 2018, now Pat. No. 10,565,977.

(51) Int. Cl.

| | | |
|---|---|---|
| *H04R 1/08* | (2006.01) | |
| *A61B 1/00* | (2006.01) | |
| *G10K 11/178* | (2006.01) | |
| *H04R 1/02* | (2006.01) | |
| *H04R 1/40* | (2006.01) | |
| *A61B 34/37* | (2016.01) | |
| *A61B 1/313* | (2006.01) | |
| *A61B 46/10* | (2016.01) | |
| *A61B 1/04* | (2006.01) | |
| *H04N 23/50* | (2023.01) | |

(52) U.S. Cl.
CPC ............ *A61B 1/3132* (2013.01); *A61B 34/37* (2016.02); *A61B 46/10* (2016.02); *G10K 11/17823* (2018.01); *H04R 1/028* (2013.01); *H04R 1/406* (2013.01); *H04R 3/005* (2013.01); *G10K 2210/116* (2013.01); *G10K 2210/3044* (2013.01); *G10K 2210/3046* (2013.01); *H04N 23/555* (2023.01)

(58) Field of Classification Search
CPC .......... H04R 1/406; H04R 3/00; H04R 3/005; A61B 1/00042; A61B 1/0004; A61B 1/04; A61B 1/3132; A61B 34/37; A61B 46/10; G10K 11/17823; G10K 2210/116; G10K 2210/3044; G10K 2210/3046; H04N 23/555
See application file for complete search history.

(56) References Cited

U.S. PATENT DOCUMENTS

| | | | |
|---|---|---|---|
| 7,395,249 B2 | 7/2008 | Wang et al. | |
| 7,758,496 B2 | 7/2010 | Abe | |
| 7,979,157 B2 | 7/2011 | Anvari | |
| 8,670,017 B2 | 3/2014 | Stuart et al. | |
| 10,565,977 B1* | 2/2020 | Miller | A61B 1/3132 |
| 2002/0071573 A1 | 6/2002 | Finn | |
| 2002/0181721 A1 | 12/2002 | Sugiyama et al. | |
| 2006/0161137 A1* | 7/2006 | Orban, III | A61B 46/10 |
| | | | 606/1 |
| 2006/0178559 A1 | 8/2006 | Kumar et al. | |
| 2007/0078303 A1 | 4/2007 | Abe | |
| 2007/0156121 A1 | 7/2007 | Millman et al. | |
| 2009/0067615 A1 | 3/2009 | Strandberg | |
| 2010/0019715 A1 | 1/2010 | Roe et al. | |
| 2010/0191375 A1 | 7/2010 | Wright et al. | |
| 2011/0218674 A1 | 9/2011 | Stuart et al. | |
| 2012/0099735 A1 | 4/2012 | Chen | |
| 2012/0327746 A1* | 12/2012 | Velusamy | G01S 5/22 |
| | | | 367/127 |
| 2013/0113929 A1 | 5/2013 | Deland | |
| 2015/0128343 A1 | 5/2015 | Katz | |
| 2016/0081753 A1* | 3/2016 | Kostrzewski | A61B 90/37 |
| | | | 606/130 |
| 2016/0089154 A1 | 3/2016 | Chien et al. | |
| 2016/0125882 A1* | 5/2016 | Contolini | H04R 3/005 |
| | | | 704/231 |
| 2017/0010671 A1 | 1/2017 | Ghaffari Toiserkan | |
| 2018/0049795 A1 | 2/2018 | Swayze et al. | |
| 2018/0049819 A1 | 2/2018 | Harris et al. | |
| 2018/0161110 A1 | 6/2018 | Overmyer et al. | |
| 2018/0168755 A1 | 6/2018 | Cagle et al. | |
| 2018/0168763 A1 | 6/2018 | Scheib et al. | |
| 2018/0185110 A1 | 7/2018 | Kumar et al. | |
| 2018/0206039 A1 | 7/2018 | Vilermo et al. | |
| 2019/0059928 A1 | 2/2019 | Nicolaescu et al. | |

FOREIGN PATENT DOCUMENTS

| | | |
|---|---|---|
| JP | 10-227849 A | 8/1998 |
| JP | 2005-118232 | 5/2005 |
| WO | 2015026697 A1 | 2/2015 |
| WO | 2017005277 | 1/2017 |

OTHER PUBLICATIONS

Extended European Search Report for European Application No. 18931001.4 dated Apr. 21, 2022, 12 pages.

* cited by examiner

SURGICAL TOOL HAVING INTEGRATED MICROPHONES

This application is a continuation of pending U.S. application Ser. No. 16/734,227, filed Jan. 3, 2020, which is a divisional of U.S. application Ser. No. 15/999,676, filed Aug. 20, 2018 (now issued as U.S. Pat. No. 10,565,977), and these applications are incorporated herein by reference in their entirety.

FIELD

Embodiments related to surgical robotic systems, are disclosed. More particularly, embodiments related to surgical robotic systems and corresponding communication devices, are disclosed.

BACKGROUND INFORMATION

Endoscopic surgery involves looking into a patient's body and performing surgery inside the body using endoscopes and other surgical tools. For example, laparoscopic surgery can use a laparascope to access and view an abdominal cavity. Endoscopic surgery can be performed using manual tools and/or robotically-assisted tools.

A surgical robotic system may be used by a surgeon to remotely command surgical tools located at an operating table. More particularly, the surgeon may use a computer console located across a room, or even across the world, from the operating table to command a robot to manipulate a surgical tool mounted on the operating table. The robotically-controlled surgical tool can be an endoscope mounted on a robotic arm. Accordingly, the surgical robotic system may be commanded by the remote surgeon to perform an endoscopic surgery.

An endoscopic surgery performed by a surgical robotic system is typically assisted by bedside staff. Although the surgeon may be remotely located, one or more bedside assistants may perform tasks at and around the operating table. For example, the bedside staff may attend to a patient or attach/detach surgical tools of the surgical robotic system. Communication between the bedside staff and the remote surgeon is essential to a successful surgery. To communicate with the remote surgeon, the bedside staff may shout across the operating arena, which may be a noisy environment. Alternatively, the bedside staff may wear and use assistive technologies, such as headsets, to communicate with the remote surgeon. Also, the bedside staff may speak into microphones affixed to something within the operating arena, e.g., a microphone hanging from a ceiling of the operating arena, to communicate with the remote surgeon.

SUMMARY

When a surgeon is not physically located at an operating table during a robotically-assisted surgery, communication between the remote surgeon and bedside staff may be difficult. Noise within the operating arena can interfere with the shouts of the bedside staff, rendering the speech inaudible. Existing assistive technologies used to facilitate communication between bedside staff and remote surgeons have several shortcomings. The use of headsets can be disruptive to a surgical workflow in the operating arena, and thus, bedside staff may forget to wear a headset or may simply opt not to wear the headset. Microphones mounted at various locations within the operating arena, e.g., hanging from a ceiling, may not extend into a zone between the operating table and the bedside staff, and thus, may not pick up the voices of the bedside staff. Similarly, the bedside staff may not face the mounted microphones, and thus, sound quality of the monitored sound may be poor.

A surgical robotic system having a communication device is provided. The communication device can include a surgical tool that integrates a microphone to face a surrounding environment, e.g., for placement between an operating table and a tableside staff. In an embodiment, the surgical robotic system includes a communication apparatus having a communication device and a user console, and the surgical tool is communicatively coupled to the user console. A remote operator, e.g., a surgeon, can use the user console to command the surgical tool. The surgical tool can include an audio system to output a voice of the remote operator to the tableside staff, and to receive a voice of the tableside staff. The voice of the tableside staff can be reproduced to the remote operator by an audio system of the user console. Accordingly, the tableside staff and the remote operator can communicate via the communication apparatus of the surgical robotic system.

In an embodiment, the surgical tool includes an endoscope. The endoscope can be attached to a robotic arm, and the robotic arm can be attached to a surgical table. The endoscope can have an elongated shaft for placement in the patient, and a housing located between a sterile barrier and the tableside staff. One or more microphones and one or more speakers can be mounted on the housing to provide the audio system to facilitate communication by the tableside staff. Several microphones of the audio system can be arranged in a microphone array to generate several microphone output signals. Optionally, a processor is mounted in the housing and can receive the microphone output signals to perform audio processing of the voice data, such as noise reduction or voice direction detection. Accordingly, the surgical tool can be used in a normal surgical workflow to provide clear communication between the tableside staff and the remote operator.

In an embodiment, the surgical tool is a sterile barrier. The sterile barrier may include a drape to be placed over a patient on the operating table, or to be placed over a robotic arm used to perform robotically-assisted surgery. More particularly, the drape may be a tubular sleeve to slip over another surgical tool and/or a portion of the robotic arm for defining a sterile zone. The other surgical tool can be attached to the robotic arm, and the robotic arm can be attached to a surgical table. The surgical tool can include a sterile adapter mounted on the tubular sleeve, and the sterile adapter can include a transmission element to transmit torque from a motor drive of the robotic arm inside of the tubular sleeve to a surgical tool outside of the tubular sleeve. One or more microphones and one or more speakers can be mounted on the sterile adapter within the sterile zone to provide an audio system to facilitate communication by the tableside staff. The audio system can be electrically connected to a data channel of the robotic arm, and thus, the remote operator can select the robotic arm to communicate to a specific region of an operating arena, e.g., to communicate to a tableside staff on a right side of the patient. Accordingly, the surgical tool can be used in a normal surgical workflow to provide clear communication between the tableside staff and the remote operator.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 1:
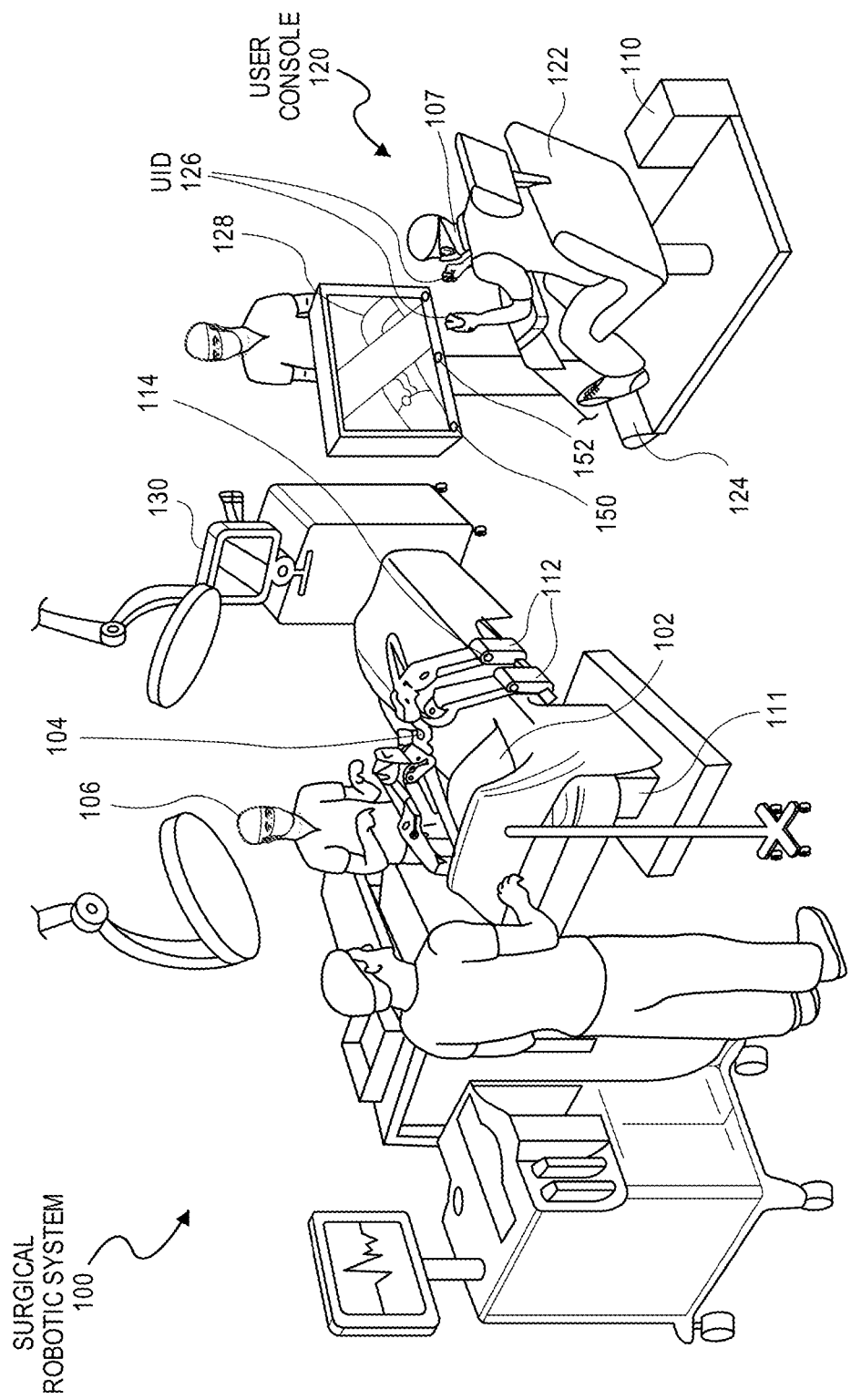
FIG. 1 is a pictorial view of an example surgical robotic system in an operating arena, in accordance with an embodiment.

Embodiments describe communication apparatuses and devices for surgical robotic systems. A communication apparatus can include a user console and a communication device that allows a remote operator, e.g., a surgeon, to communicate with bedside staff located at an operating table. The communication device can facilitate communication through an audio system integrated in surgical tools that are in use at the operating table. For example, the surgical tools may include endoscopes or sterile barriers having integrated microphones and/or speakers, as described below. The communication device may, however, include audio systems incorporated into other surgical tools, such as cytoscopes, laparascopes, or arthroscopes, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., in a direction of a patient being operated on during a surgery. Similarly, "proximal" may indicate a location in a second direction opposite to the first direction, e.g., in a direction away from the patient. Such terms are provided to establish relative frames of reference, however, and are not intended to limit the use or orientation of a communication device or surgical robotic system to a specific configuration described in the various embodiments below.

In an aspect, communication devices including surgical tools incorporating audio systems that can be located within a sterile area of an operating arena are provided. More particularly, a communication device can include a surgical tool that incorporates one or more microphone(s) or speaker(s). The microphone(s) or speaker(s) can face a surrounding environment, e.g., may be located between a sterile barrier on an operating table and surrounding bedside staff, during a surgery. The microphone(s) or speaker(s) may be mounted on a proximal portion of a device, such as on a housing of an endoscope that is opposite to a distal end of the endoscope that inserts into a patient, or on a sterile adapter of a sterile barrier, to pick up the voice of the bedside staff working around the operating table while the surgical tools are in use. In another aspect, the surgical tools are used as part of the normal workflow of the surgery, and thus, the use of the surgical tools in the communication devices to facilitate communications between the bedside staff and the remote surgeon is inherent in the process flow. More particularly, the microphone(s) or speaker(s) are integrated directly into the surgical tools used to operate on a patient, and thus, the audio transducers can be naturally located between the operating table and the bedside staff during a surgery.

Referring to FIG. 1, this is a pictorial view of an example surgical robotic system in an operating arena. A surgical robotic system 100 includes a user console 120, a control tower 130, and one or more surgical robotic arms 112 at a surgical robotic platform 111, e.g., a table, a bed, etc. The surgical robotic system 100 can incorporate any number of devices, tools, or accessories used to perform surgery on a patient 102. For example, the surgical robotic system 100 may include a communication device or a communication apparatus to facilitate vocal communications between surgeons and tableside staff. The communication device or communication apparatus can include one or more surgical tools 104 used to perform surgery. A surgical tool 104 may have an end effector, and may attach to a distal end of a robotic arm 112, for executing a surgical procedure. Surgical tool 104 may not be attached to robotic arm 112, e.g., surgical tool 104 may be a sterile barrier, as described below.

Each surgical tool 104 may be manipulated manually, robotically, or both, during the surgery. For example, surgical tool 104 may be a tool used to enter, view, or manipulate an internal anatomy of patient 102, or surgical tool 104 can be a grasper that can grasp tissue of patient 102. Surgical tool 104 may be handled manually, by a tableside staff 106; or it may be controlled robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user interface devices, UIDS 126, and at least one user display 128 that is configured to display, for example, a view of the surgical site inside patient 102. In the example user console 120, remote operator 107 is sitting in seat 122 and viewing the user display 128 while manipulating a foot-operated control 124 and a handheld UID 126 in order to remotely command the arms 112 and surgical tools 104 (that are mounted on the distal ends of the arms 112). Foot-operated control(s) 124 can be foot pedals, such as seven pedals, that generate motion control signals when actuated. User console 120 may include one or more additional interface devices (FIG. 10), such as a microphone, keyboard, or a joystick, to receive inputs to command operations of user console 120 or surgical robotic system 100.

In some variations, tableside staff 106 may also operate system 100 in an "over the bed" mode, in which tableside staff 106 (user) is now at a side of patient 102 and is simultaneously manipulating a robotically-driven tool (end effector attached to arm 112), e.g., with a handheld UID 126 held in one hand, and a manual laparoscopic tool. For example, the tableside staff's left hand may be manipulating the handheld UID 126 to command a robotic component, while the tableside staff's right hand may be manipulating a manual laparoscopic tool. Thus, in these variations, tableside staff 106 may perform both robotic-assisted minimally invasive surgery and manual laparoscopic surgery on patient 102.

During an example procedure (surgery), patient 102 is prepped and draped in a sterile fashion to achieve anesthesia. Initial access to the surgical site may be performed manually while the arms of the surgical robotic system 100 are in a stowed configuration, e.g., under platform 111, or a withdrawn configuration (to facilitate access to the surgical site). Once access is completed, initial positioning or preparation of the surgical robotic system including its arms 112 may be performed. Next, the surgery proceeds with the remote operator 107 at the user console 120 utilizing the foot-operated controls 124 and the UIDs 126 to manipulate the various end effectors and perhaps an imaging system, to perform the surgery. Manual assistance may also be provided at the procedure bed or table, by sterile-gowned bedside personnel, e.g., tableside staff 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in surgical robotic system 100. UID 126 may be communicatively coupled to the rest of surgical robotic system 100, e.g., via a console computer system 110. UID 126 can generate spatial state signals corresponding to movement of UID 126, e.g., position and orientation of the handheld housing of the UID, and the spatial state signals may be input signals to control a motion of the robot arm actuator 114. Surgical robotic system 100 may use control signals derived from the spatial state signals, to control proportional motion of actuator 114. In one embodiment, a console processor of console computer system 110 receives the spatial state signals and generates the corresponding control signals. Based on these control signals, which control how the actuator 114 is energized to move a segment or link of arm 112, the movement of a corresponding surgical tool 104 that is attached to the arm may mimic the movement of UID 126. Similarly, interaction between remote operator 107 and UID 126 can generate for example a grip control signal that causes a jaw of a grasper of surgical tool 104 to close and grip the tissue of patient 102.

Surgical robotic system 100 may include several UIDs 126, where respective control signals are generated for each UID that command the actuators and the surgical tool (end effector) of a respective arm 112. For example, remote operator 107 may move a first UID 126 to command the motion of actuator 114 that is in a left robotic arm, where the actuator responds by moving linkages, gears, etc., in that arm 112. Similarly, movement of a second UID 126 by remote operator 107 commands the motion of another actuator 114, which in turn moves other linkages, gears, etc., of the surgical robotic system 100. Surgical robotic system 100 may include a right arm 112 that is secured to the bed or table to the right side of the patient, and a left arm 112 that is at the left side of the patient. An actuator 114 may include one or more motors that are controlled so that they drive the rotation or linear movement of a joint of arm 112, to for example change, relative to the patient, an orientation of an endoscope or a grasper of the surgical tool that is attached to that arm. Motion of several actuators 114 in the same arm 112 can be controlled by the spatial state signals generated from a particular UID 126. UIDs 126 can also command motion of respective surgical tool graspers. For example, each UID 126 can generate a respective grip signal to control motion of an actuator, e.g., a linear actuator, that opens or closes jaws of the grasper at a distal end of the surgical tool to grip tissue within patient 102.

In some aspects, the communication between platform 111 and user console 120 may be through a control tower 130, which may translate user commands that are received from user console 120 (and more particularly from console computer system 110) into robotic control commands that are transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Surgical robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

As described above, surgical tool 104 may be a tool used to facilitate surgery. Surgical tool 104 can be a tool to actively enter, view, or manipulate an internal anatomy of patient 102. In an embodiment, surgical tool 104 is a video imaging device. For example, surgical tool 104 can include an endoscope (FIG. 2) used to perform endoscopic surgery. The endoscope can be manually handled by tableside staff 106. For example, tableside staff 106 may mount the endoscope onto a robotic arm 112 of surgical robotic system 100. Tableside staff 106 may also detach the endoscope from robotic arm 112 to manually handle an orientation or a location of surgical tool 104. Thus, beside operator 106 or robotic arm 112 can move and manipulate the endoscope to perform surgery on patient 102.

In an embodiment, surgical tool 104 is a surgical instrument for manipulating tissue. Surgical tool 104 can include a grasper or another component to engage and manipulate tissue. For example, the surgical instrument can be manually handled by tableside staff 106 or mounted on robotic arm 112 to grasp and manipulate tissue.

Surgical tool 104 can be a tool that remains outside of patient 102 to facilitate surgery. In an embodiment, surgical tool 104 is a sterile barrier (FIG. 7) to define a sterile zone of a surrounding environment. Tableside staff 106 may place the sterile barrier over patient 102 to form the sterile zone within the surrounding environment. For example, the sterile zone may include a region of the surrounding environment between the sterile barrier and tableside staff 106. In an embodiment, surgical tool 104 includes a sterile adapter, as described below, and a microphone can be mounted on the sterile adapter.

User console 120 may be telecommunicatively coupled to a communication device having surgical tool 104 to exchange audio data. That is, audio data may be exchanged between user console 120 and surgical tool 104 to allow remote operator 107 to converse with tableside staff 106. In an embodiment, an audio transducer, e.g., a microphone or a speaker, is mounted on a portion of surgical tool 104 to receive a voice of tableside staff 106 or emit sound output to tableside staff 106. A portion of surgical tool 104 can be between a surgical drape placed over patient 102 and the surrounding environment. By contrast, a distal portion of surgical tool 104 may be between the drape and operating table 111, e.g., within patient 102. In an embodiment, the audio transducer is mounted on the portion between a sterile barrier and tableside staff 106. Thus, sound propagating toward patient 102 from tableside staff 106 within the sterile zone can be picked up by the audio transducer. Similarly, sound emitted by the audio transducer can propagate through the sterile zone and be heard by tableside staff 106.

In an embodiment, the audio transducer is an acoustoelectric transducer, e.g., a microphone, to convert a sound input, e.g., the voice of tableside staff 106, into an audio signal, e.g., a microphone output signal. The microphone output signal can be an electrical signal that is processed by and/or transmitted from surgical tool 104 to computer system 110 of user console 120. As described below, the microphone output signal may encode audio data to be communicated by a wired or wireless connection between surgical tool 104 and user console 120. Accordingly, user console 120 may receive the microphone output signal, and one or more console speakers 150 mounted on user console 120 can receive the microphone output signal from processor 302. Console speaker(s) 150 can convert the microphone output signals into a sound output. The sound output may reproduce the speech from tableside staff 106 to be heard by remote operator 107.

Audio communication between user console 120 and surgical tool 104 may be two-way. For example, a console microphone 152 mounted on user console 120 may receive a sound input, e.g., a voice, from remote operator 107 at user console 120. Console microphone 152 can convert the sound input from the user into an audio signal encoding the voice data. User console 120 can be in communication with robotic arm 112 and/or the communication device having surgical tool 104, and accordingly, the voice data may be exchanged between computer system 110 and surgical tool 104 via an electrical communication connection. In an embodiment, an audio transducer of surgical tool 104 is an electroacoustic transducer, e.g., a speaker, to convert the electrical voice signals into a sound output reproducing the speech of remote operator 107 to be heard by tableside staff 106. Accordingly, remote operator 107 and tableside staff 106 may communicate clearly even when tableside staff 106 is not facing remote operator 107.

Remote surgical tool 104 may be another surgical tool or accessory integrating a microphone or speaker to be located between the sterile barrier and tableside staff 106 within the surgical arena. For example, surgical tool 104 may be a sterile barrier having a drape covering a portion of surgical robotic system 100 or patient 102. The sterile barrier can integrate a microphone on an external surface facing away from patient 102 and facing the surrounding environment. In an embodiment, the drape of the sterile barrier is a sleeve to be placed over robotic arm 112 of surgical robotic system 100. As described below, the sleeve may include a sterile adapter to allow robotic arm 112 to transmit mechanical forces to another surgical device, e.g., an endoscope, mounted on the robotic arm. A microphone or speaker may be mounted on an external surface of a portion of the sleeve, e.g., the sterile adapter, to receive or emit sound within the space between the sterile barrier and tableside staff 106.

Figure 2:
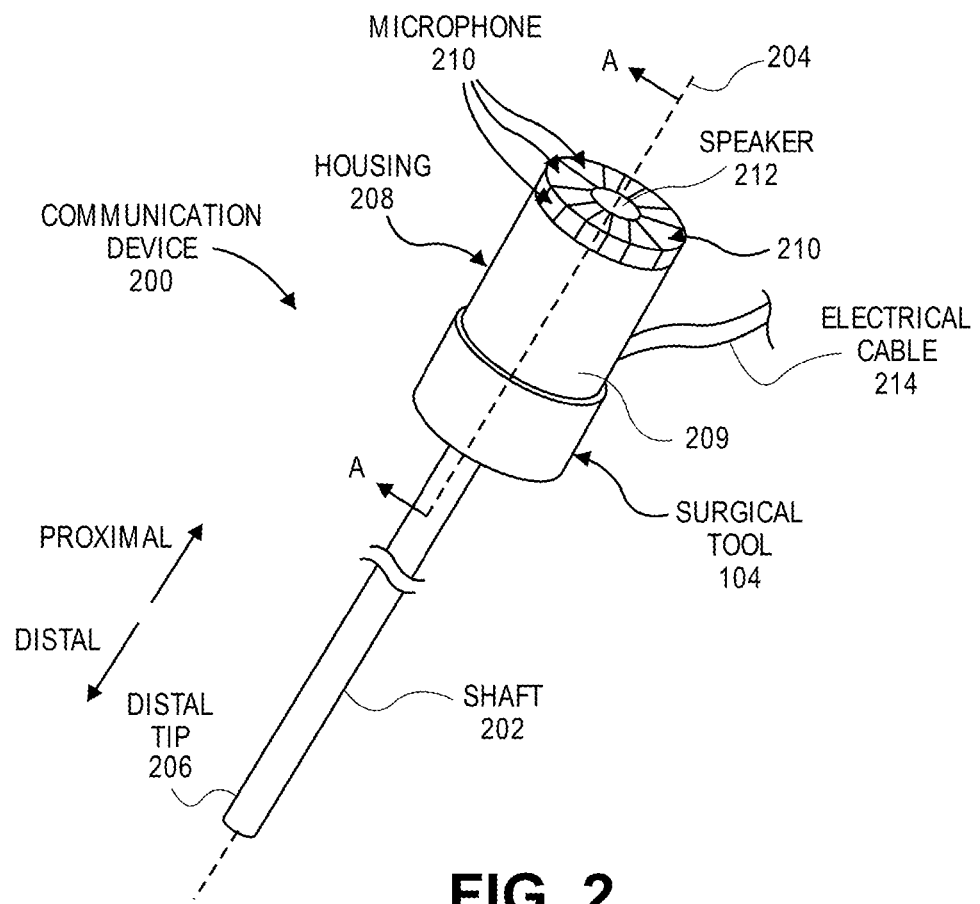
FIG. 2 is a perspective view of a communication device, in accordance with an embodiment.

Referring to FIG. 2, a perspective view of a communication device is shown in accordance with an embodiment. A communication device 200 in surgical robotic system 100 can be used to facilitate vocal communications between surgeons 107 and tableside staff 106. Communication device 200 can include a surgical tool 104. In an embodiment, surgical tool 104 is a video imaging device. For example, the video imaging device can include an endoscope, such as a laparoscope. In an embodiment, the endoscope is a manual surgical tool. More particularly, the endoscope may be intended to be held and manipulated by an operator, and not a surgical robotic system. The endoscope can include a proximal portion to be held by the operator, and a distal portion extending longitudinally from the proximal portion. The distal portion is to be inserted into patient 102. Accordingly, the distal portion can be within a space between a sterile barrier and operating table 111 (e.g., within patient 102) during surgery, and the proximal portion can be external to the sterile barrier, such as between the sterile barrier and tableside staff 106.

Surgical tool 104 can include an elongated shaft 202 extending longitudinally along a central axis 204. Shaft 202 can be rigid or flexible. For example, shaft 202 can be a rigid metallic tube extending to a distal tip 206. Distal tip 206 may be straight or angled to allow the operator to direct distal tip 206 toward a target anatomy. Distal tip 206 can be inserted into the target anatomy. Furthermore, distal tip 206 can be actuatable to change a shape of distal tip 206 from a straight tip to an angled tip. More particularly, the endoscope may include controls, such as tension cables, that can be actuated to transition distal tip 206 from a straight configuration to a curved configuration.

In an embodiment, an optical subsystem (not shown) is mounted on distal tip 206. The optical subsystem can include an endoscope camera. The optical subsystem can include one or more of an objective lens, a charge-coupled device, an illumination lens, or a light-emitting diode. Accordingly, the optical subsystem can illuminate an interior anatomy of patient 102 and obtain visual data of, i.e., view, the interior anatomy. The vision data can be transmitted from the optical subsystem through shaft 202 by corresponding circuitry.

Surgical tool can include a housing 208 mounted on shaft 202 proximal to distal tip 206. For example, housing 208 may be coupled to a proximal end 350 (FIG. 3) of shaft 202. Shaft 202 may extend into housing 208. For example, proximal end 350 of shaft 202 can be a region of shaft 202 opposite from distal tip 206, and may be surrounded by electronic housing walls. Housing 208 can have any shape. In an embodiment, housing 208 includes a cylindrical portion having an outer surface 209 around central axis 204. More particularly, outer surface 209 may be symmetrically disposed about central axis 204. For example, outer surface 209 may have a circular profile centered on central axis 204. Housing 208 can be located along central axis 204 external to the sterile barrier, and thus, outer surface 209 may face the surrounding environment around central axis 204. Accordingly, a wall of housing 208 having outer surface 209 can provide a useful mounting surface to hold an audio transducer of the endoscope.

One or more microphones 210 may be mounted on an outer surface of surgical tool 104. For example, one or more microphones may be mounted on housing 208. In an embodiment, several microphones 210 are mounted on outer surface 209 of housing 208. Microphone(s) 210 can be at a proximal end of housing 208 or along a sidewall of housing 208. During a surgery, microphone(s) 210 can be operatively disposed above a sterile barrier, and accordingly, microphone(s) 210 can be in front of tableside staff 106 during the surgery. For example, the sterile barrier can cover portions of surgical robotic system 100, and surgical tool 100 can be mounted on an opposite side of sterile barrier from the covered portions. Similarly, the sterile barrier can cover patient 102, and a distal end of shaft can be inserted into patient 102 through a hole in the sterile barrier, while proximal end 350 remains located above the sterile barrier. Accordingly, microphone(s) 210 can receive a sound input, e.g., a voice of tableside staff 106, and convert the sound input into respective audio signals, e.g., microphone output signals. The sound input can be used for various purposes, including voice control of surgical robotic systems, transcription, and telemonitoring.

In an embodiment, the endoscope includes several microphones 210 arranged in a microphone array. More particularly, the microphone array can include at least two microphones 210. The microphone array can facilitate several advantageous audio functions. For example, the microphone array can allow the endoscope to perform noise reduction and/or to determine a direction of a sound source, as described below. When several microphones 210 are integrated in surgical tool 104, the microphones can generate several microphone output signals that may be processed to provide such functionality.

The endoscope may include one or more speakers 212. Speaker(s) 212 can be mounted on outer surface 209 of housing 208. A single speaker 212 can be mounted on a proximal end of housing 208 on central axis 204. For example, outer surface 209 may have a cylindrical sidewall extending parallel to central axis 204 and intersecting an end wall extending transverse to central axis 204, and speaker 212 may be mounted on the end wall such that central axis 204 extends through speaker 212. Several microphones 210 may be arranged around the single speaker 212 on outer surface 209. The microphones 210 may be on the sidewall and/or the end wall of outer surface 209, e.g., arranged along an edge of an intersection of the sidewall and the end wall. Several speakers 212 may be mounted along the sidewall of housing 208 around central axis 204, e.g., in a speaker array. Like microphone(s) 210 of the endoscope, speaker(s) 212 may be located between the sterile barrier and tableside staff 106 during a surgery, and thus, speaker(s) 212 may receive an acoustic output signal and convert the acoustic output signal into a sound output to be heard by tableside staff 106. The sound output can be a voice of remote operator 107, an alarm, an alert, etc.

Microphone output signal generated by microphone 210 and acoustic output signal received by speaker 212 may be processed and transmitted via circuitry, which can optionally be within housing 208 or at another location, such as within user console 120 or control tower 130. The electrical signals representing audio data can be communicated outside of housing 208 through a wired or wireless connection. In an embodiment, an electrical cable 214 is attached to housing 208 to exchange electrical signals between housing 208 and user console 120 (and/or control tower 130). The electrical signals can be power or data signals, and thus, electrical cable 214 may include one or more of a power wire or a data wire. Electrical cable 214 may carry information between surgical tool 104, e.g., from the endoscope, and user console 120

Figure 3:
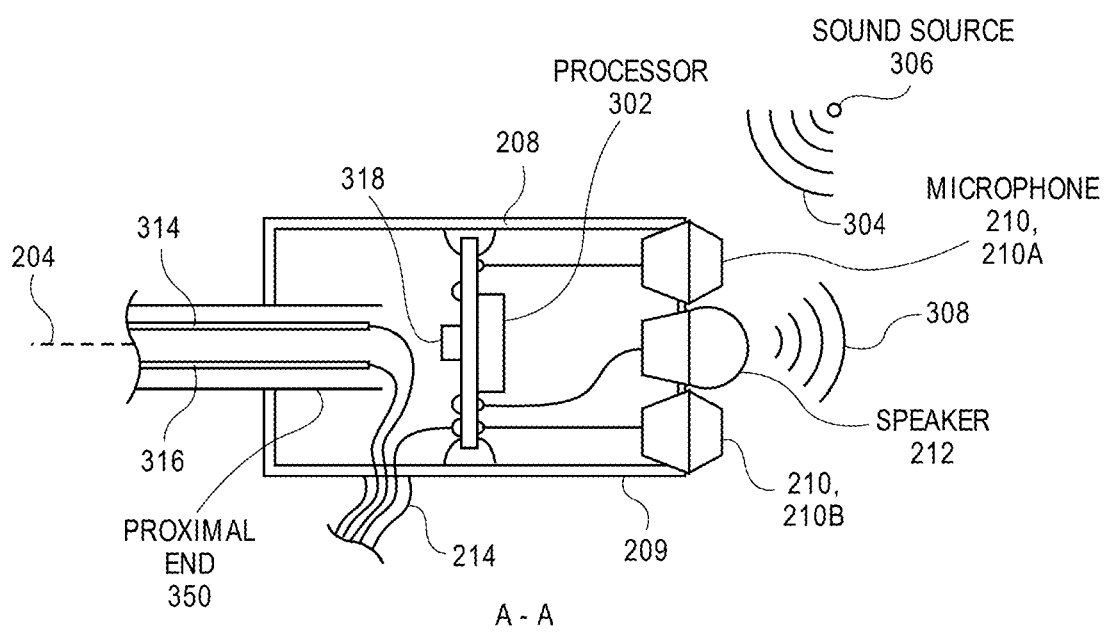
FIG. 3 is a cross-sectional view, taken about line A-A of FIG. 2, of a housing of a surgical tool, in accordance with an embodiment.

Referring to FIG. 3, a cross-sectional view, taken about line A-A of FIG. 2, of a housing of a surgical tool is shown in accordance with an embodiment. Electrical signals transmitted through electrical cable 214 may originate from or be received by a processor 302, which may optionally be located in housing 208. Alternatively, processor 302 may be remotely located, e.g., within user console 120 or control tower 130, and may be in signal communication with the electronics of the endoscope, e.g., microphone(s) 210 or speaker(s) 212. For example, processor 302 can be communicatively coupled, e.g., electrically connected, to microphone(s) 210 of the endoscope to receive microphone output signals generated by microphone(s) 210 in response to an impinging sound input 304 from a source 306, e.g., tableside staff 106. Similarly, processor 302 can be communicatively coupled, e.g., electrically connected, to speaker(s) 212 to output an acoustic output signal to speaker(s) 212. The acoustic output signal can be an audio signal received by processor 302 from another sound input, such as from a user at user console 120. Speaker(s) 212 can receive the acoustic output signal and convert the audio signal into a sound output 308. Processor 302 can process and transmit audio signals such as microphone output signals of microphone(s) 210 and acoustic output signals of speaker(s) 212. For example, processor 302 can be communicatively coupled to microphone(s) 210 of surgical tool 104 and microphone(s) 152 of user console 120, and can process and transmit respective audio signals generated by the microphone(s) to facilitate vocal communication between tableside staff 106 and the user at user console 120. Processor 302 can perform several audio processing functions to enhance such communications between remote operator 107 and tableside staff 106, as described below.

In an embodiment, processor 302 may incorporate analog or digital signal processing components to reduce unwanted environmental noise. More particularly, processor 302 may receive microphone output signals from one or more microphones 210 to perform noise reduction. In an embodiment, microphone 210 is located on outer surface 209 of housing 208 to receive sound input 304 from source 306. Microphone 210 can receive sound input 304 from source 306 and convert the sound into an audio signal that is provided to signal processing circuitry of processor 302. Processor 302 can process the audio signal to measure a background noise in the signal. For example, processor 302 can detect and measure ambient sound from the surrounding environment, beeping sounds coming from electronics within the operating arena, fan noise, etc. Processor 302 can perform noise reduction algorithms on the audio signal to reduce the background noise in the signal. The modified signal can be output by processor 302 to transmit a clear acoustic signal to user console 120 for reproduction to remote operator 107.

Processor 302 may incorporate analog or digital signal processing components to determine a direction of source 306 of sound input 304. In an embodiment, central axis 204 extends through housing 208 and several microphones 210 are mounted on outer surface 209 around central axis 204. For example, several microphones 210 may be arranged symmetrically about central axis 204 to form a microphone array. The microphone(s) in the array can be arranged equidistantly with each other in a plane. For example, the plane may extend perpendicular to central axis 204 and/or shaft 202 such that the equidistantly spaced microphones on the plane form a ring around central axis 204. The microphone array can be mounted on the outer surface of housing 208 and oriented to face a particular direction. For example, the array can be located on a proximal end wall of housing 208 such that each microphone 210 faces a proximal direction. By way of example, each microphone 210 may have a diaphragm having a plane that is oriented within 45-90 degrees from central axis 204 to receive sound propagating toward housing 208 from the surrounding environment.

In an embodiment, processor 302 processes audio signal(s) from each of the microphone(s) 210 in the array to detect an acoustic location of sound source 306. for example, processor 302 can determine a distance and/or direction of sound source 306 relative to surgical tool 104. Detection of the source location can be performed actively or passively. In an embodiment, detection of the source location is passive, and includes detection based on a time difference of arrival at several microphone(s) 210. For example, the respective diaphragms of each microphone 210 in the microphone array can be located and/or directed differently such that an impinging sound, e.g., sound input 304, excites a different response in each microphone 210. For example, primary microphone 210A may be nearer to and/or facing source 306 more as compared to secondary microphone 210B. Accordingly, primary microphone 210A may generate a first microphone output signal based on its position relative to the sound source and secondary microphone 210B may generate a second microphone output signal based on its position relative to the sound source. Signal processing circuitry of processor 302 can perform direction of arrival processing on the microphone output signals to detect a direction of arrival of sound input 304. For example, processor 302 can use a cross-correlation function between the first microphone output signal and the second microphone output signal to determine a direction of source 306. More particularly, the microphone array can generate several microphone output signals that may be differentiated to detect voice directionality within the operating arena. For example, source direction information can be used to determine a location or direction within the operating arena at which tableside staff 106 is located.

It will be appreciated that a number of microphones 210 in the microphone array corresponds to a number of microphone output signals that may be processed by processor 302. Processor 302 may use these signals for different purposes. For example, at least two microphone(s) 210 can output at least two signals that may be used to detect the direction of arrival of a sound from a sound source in a two-dimensional plane. By contrast, at least three microphone(s) 210 can output at least three signals that may be used to detect the direction of arrival of the sound from a sound source in a three-dimensional space. In an embodiment, processor 302 can determine a location of the sound source based on the signals output by three or more microphones 210. For example, microphone output signals from three or more microphones 210 can be used to perform triangulation processing to determine the location of the sound source in the operating arena.

Detection of a source of sound and a direction of the source can improve communication between the user at user console 120 and tableside staff 106 in the operating arena. For example, when the source location is known, processor 302 can emphasize sound pick up in the detected direction of arrival of sound input 304, using a beam forming algorithm. The beam forming algorithm can, for example, increase a gain of microphone(s) 210 toward the source location. Processor 302 can also emphasize speech of a particular operator after detecting the source locations. For example, the speech of the particular operator can be sound input 304, and processor 302 can identify the speech as coming from the particular operator. Thereafter, processor 302 can detect the speech from the particular operator as part of a direction of arrival processing, and beam form sound communications toward the particular operator as the operator moves about the operating arena. The voices of other operators, or of other sounds such as beeps or fan noise in the surrounding environment, can be deemphasized by processor 302. Similarly, sound output from speaker(s) 212 can be controlled to beam sound toward the source location. Accordingly, communication between the user at user console 120 and tableside staff 106 in the operating arena can be improved.

Housing 208 may contain electronics circuitry corresponding to non-audio functionalities of the endoscope. For example, application-specific circuitry may include image sensing circuitry or orientation sensing circuitry in one or more integrated circuits optionally mounted within housing 208. In an embodiment, processor 302 is mounted on a circuit board within housing 208. The circuit board may exchange electrical signals with the optical subsystem at distal tip 206.

In an embodiment, the optical subsystem at distal tip 206 exchanges electrical and/or optical signals directly with control tower 130. More particularly, optical fibers can run from control tower 130 through a sheathing of electrical cable 214, or through a dedicated optical cable, to the cameras on distal tip 206 of the endoscope. For example, the endoscope may include an efferent electrical and/or optical connector 314 to carry electrical or optical signals to the optical subsystem, and an afferent electrical connector 316 to carry electrical or optical signals from the optical subsystem. Efferent electrical or optical signals can include control signals to control illumination or focal parameters of the optical subsystem and afferent electrical signals can encode image data of anatomical images captured by the optical subsystem.

In an embodiment, the endoscope may be used for laparoscopic surgery and one or more orientation sensors or tracking technologies may be incorporated in the endoscope to determine position and orientation information during the surgery. Surgical tool 104 can include an inertial measurement unit (IMU) 318 having an accelerometer to generate an orientation signal of a body attached to IMU 318. IMU 318 may be mounted within housing 208. IMU 318 can be attached to the circuit board and can be electrically connected to processor 302. Thus, IMU 318 may be fixed relative to housing 208, and IMU 318 may generate an orientation signal corresponding to a position or orientation of housing 208 in space. IMU 318 may transmit the orientation signal to processor 302, and processor 302 may determine an orientation of housing 208 based on the orientation signal.

The determined orientation can be used for several purposes. For example, the orientation signal can be used to determine whether tableside staff 106 has laid surgical tool 104 on a surgical drape when using surgical tool 104 in a manual mode, e.g., when performing surgical operations when holding surgical tool 104 by hand. The orientation signal from IMU 318 can be used to determine which portion of the microphone array 210 to activate to listen to a user. For example, the orientation signal can be used to determine the microphones 210 of the array that are facing the bed or are near drapes, and thus, those microphones can be disabled to direct the microphone pickup toward the voices in the operating arena, e.g., the microphones 210 nearest to the user can be activated for listening. Similarly, the orientation signal from IMU 318 can be used to determine a direction to focus a sound output from one or more speakers 212. For example, the orientation signal can be used to determine the speakers 212 of an array that are facing away from the bed or drapes and toward the operating arena. Accordingly, those speakers can be activated to output sound to the nearby tableside staff 106, and not toward the bed or drapes.

Microphone 210 and speaker 212 of surgical tool 104 may be sterilizable. More particularly, the components of microphone 210 and speaker 212, e.g., a diaphragm, surround, voicecoil, etc., may be sterilizable by low temperature sterilization processes. The processes may heat surgical tool 104 to a temperature of 135 degrees Fahrenheit without damaging the components of microphone 210 and speaker 212. Accordingly, surgical tool 104 may be sterilized and reused without replacing the speaker or microphone components.

Figure 4:
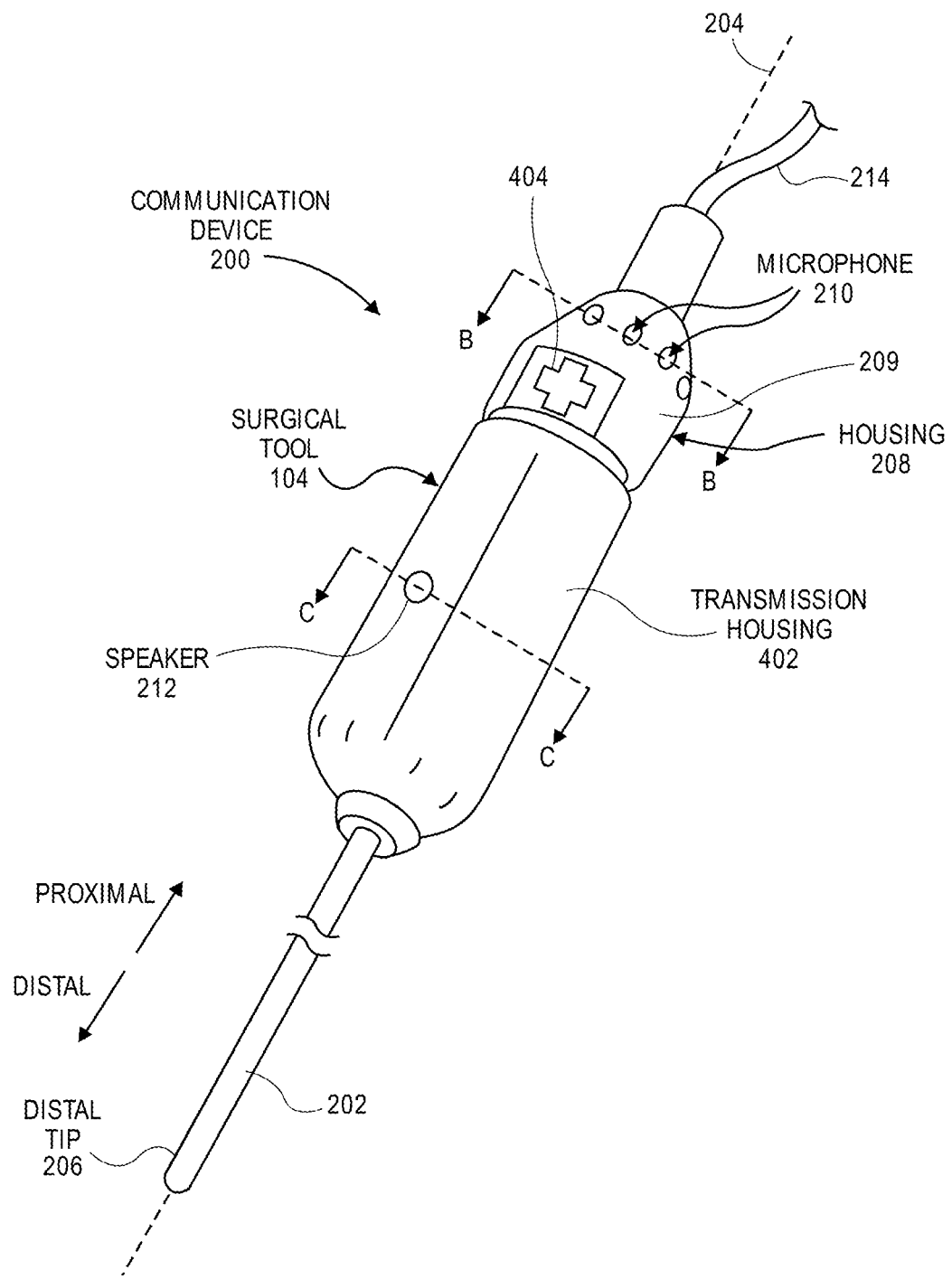
FIG. 4 is a perspective view of a communication device, in accordance with an embodiment.

Referring to FIG. 4, a perspective view of a communication device is shown in accordance with an embodiment. In an embodiment, surgical tool 104 of communication device 200 may include a robotically-controlled endoscope. More particularly, the position or orientation of the endoscope may be manipulated by another component of surgical robotic system 100, such as by robotic arm 112. In an embodiment, surgical tool 104 includes a transmission housing 402 mounted on shaft 202. Transmission housing 402 may interface with robotic arm 112. That is, transmission housing 402 may connect directly or indirectly with robotic arm 112, e.g., through a sterile adapter component, as described below. Transmission housing 402 can contain a mechanical transmission used to convert a mechanical input from surgical robotic system 100 into a mechanical output of the endoscope. For example, the mechanical transmission can drive rotation of shaft 202 or can actuate an end effector (not shown) mounted at distal tip 206 of shaft 202.

A relative orientation between transmission housing 402 and housing 208 can be different in different embodiments. For example, transmission housing 402 can be mounted on shaft 202 distal to housing 208 along central axis 204. That is, transmission housing 402 may be closer to the distal tip 206 than housing 208. Alternatively, housing 208 may be distal to transmission housing 402, e.g., nearer to distal tip 206. In either case, housing 208 may move relative to transmission housing 402. For example, central axis 204 may extend through transmission housing 402 and housing 208, and housing 208 may be rotatable about central axis 204 relative to transmission housing 402. Rotation of housing 208 may be caused by a torque applied to shaft 202 by a transmission element contained in transmission housing 402. That is, transmission element(s) within transmission housing 402 can produce relative rotational motion between transmission housing 402 and housing 208. Accordingly, transmission housing 402 may remain fixed in space relative to an end of robotic arm 112 while housing 208 and shaft 202 rotate about central axis 204 to change an orientation of distal tip 206 within patient 102 during a surgery.

The endoscope can include a manual input control 404 to allow tableside staff 106 to control a function of the endoscope. Manual input control 404 may include one or more of a button, a scroll wheel, or a switch that tableside staff 106 can actuate as a control input to processor 302. By way of example, tableside staff 106 may press a button to trigger one or more of the audio, vision, or mechanical subsystems of the endoscope. In an embodiment, tableside staff 106 can actuate manual input control 404 to enable communication between the endoscope and user console 120. For example, a transceiver of the endoscope can be in a receive mode, and when tableside staff 106 wants to talk to operator 107, a "push-to-talk" button can be pressed to switch the transceiver to a transmit mode for communicating signals generated by microphones 210 to user console 120.

In an embodiment, several microphones 210 are mounted on housing 208 around central axis 204. For example, microphones 210 may be arranged symmetrically about central axis 204 on outer surface 209 of housing 208. Similarly, one or more speakers 212 may be mounted on transmission housing 402, e.g., along an external wall of transmission housing 402. Accordingly, when housing 208 rotates relative to transmission housing 402, the microphone array on housing 208 may rotate relative to speaker 212 on transmission housing 402. The movement of microphones 210 can be compensated for by one or more of a structure or an audio processing algorithm of the endoscope.

Figure 5:
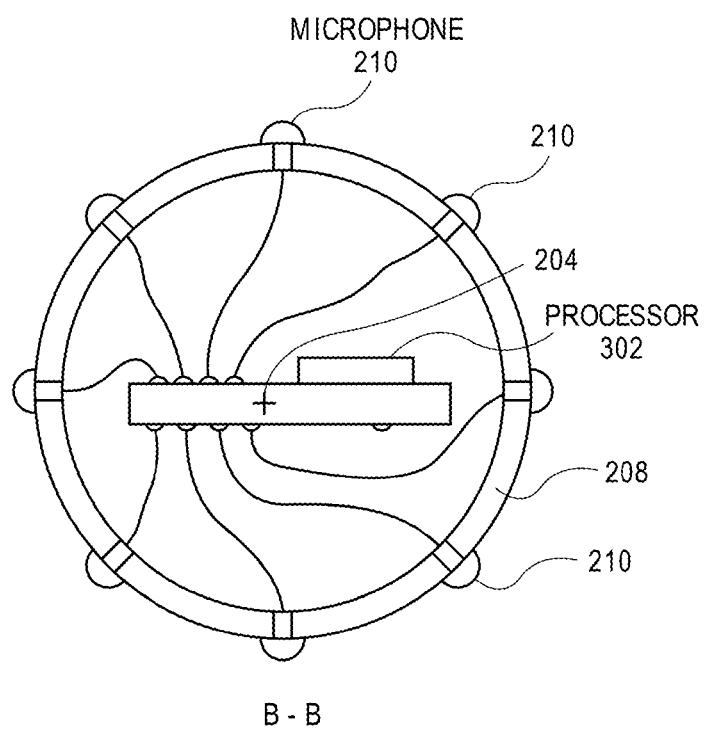
FIG. 5 is a cross-sectional view, taken about line B-B of FIG. 4, of a housing of a surgical tool, in accordance with an embodiment.

Referring to FIG. 5, a cross-sectional view, taken about line B-B of FIG. 4, of an housing of a surgical tool is shown in accordance with an embodiment. The structure of the endoscope may compensate for microphone movement. Microphones 210 may be symmetrically disposed about central axis 204. For example, when the microphone array includes eight microphones 210, each microphone may be located at a 45 degree angle (measured within a plane transverse to central axis 204) relative to a pair of adjacent microphones 210. Accordingly, the field of audition for each microphone 210 may be approximately the same. Microphones 210 can be positionally balanced or evenly distributed about the central axis 204.

The audio processing algorithm of the endoscope can compensate for microphone movement by tracking a position of each microphone 210 within a frame of reference. When a first microphone 210 is directed toward a sound source 306, a position of the sound source within a fixed frame of reference, e.g., the operating arena, may be known. As the first microphone 210 rotates away from the sound source 306 and a second microphone 210 rotates toward the sound source 306, the angle of rotation of the microphones 210 relative to the fixed frame of reference can be tracked. For example, processor 302 can monitor a shaft encoder to determine a rotational orientation of housing 208 about central axis 204. The rotational orientation can be used to change a parameter of the microphone output signals. For example, the microphone output signal from the microphone rotating into alignment with the sound source may be used as a primary microphone output signal in a noise reduction algorithm and the microphone output signal from the microphone rotating away from the sound source may be used as a secondary microphone output signal in the noise reduction algorithm.

As described above, orientation data from the endoscope may also be used to direct the microphone pickup and/or designate primary and secondary microphones 210A, 210B. For example, orientation data from IMU 318 can be processed to determine a relative orientation between microphone(s) 210 and a surrounding environment. Similarly, arm tracking data generated by the robotics system for tracking and positioning arms 112 within the operating arena can be used to determine an orientation of the endoscope within the operating arena. When the orientation of the endoscope is known, a position and direction of microphone(s) 210 can be determined. Accordingly, the microphone(s) 210 which are directed toward a region of interest can be activated to listen to the region and/or the primary and secondary microphones 210A, 210B can be designated for noise reduction processing.

The audio processing algorithms can also be used to optimize audio quality based on movement of the endoscope as a whole. The endoscope position and orientation may be controlled by a surgical robotic system under the command of user console 120. For example, remote operator 107 may command movement of robotic arm 112 through input commands entered in user console 120, and thus, the position and orientation of the endoscope may be determined through robotics kinematics. Placement of microphones 210 and speakers 212 on the endoscope are known, and thus, a position and orientation of microphone 210 and/or speaker 212 may also be determined through kinematic algorithms. Audio processing algorithms may account for placement of microphone 210 and/or speaker 212 by optimizing audio parameters of the audio transducers based on position. For example, amplifier gains or other parameters may be modified to account for the position of the audio transducers. That is, a gain of microphone 210 and/or speaker 212 known to be facing tableside staff 106 may be increased compared to a gain of an audio transducer not facing tableside staff 106. In this way, audio processing algorithm may allow remote operator 107 to select speakers 212 or microphones 210 to focus communication with one of several tableside staff 106 in the operating arena.

The selection of an intended tableside staff 106 by remote operator 107 may cause robotic arm 112 to orient the endoscope in a manner that places an audio transducer at an optimal location. For example, when a single speaker 212 is mounted on transmission housing 402, robotic arm 112 may twist the endoscope to direct the speaker 212 toward the intended tableside staff 106.

The audio processing algorithm can also adjust to account for a decrease in audio performance due to movement of the endoscope. For example, movement of robotic arm 112 can generate noise that does not provide useful information to remote operator 107. When robotic arm 112 moves the endoscope, audio pick up by microphone 210 of the endoscope may be turned off or an audio gain of microphone 210 may be reduced. The noise reduction may reduce the likelihood of distracting remote operator 107 with noise.

Figure 6:
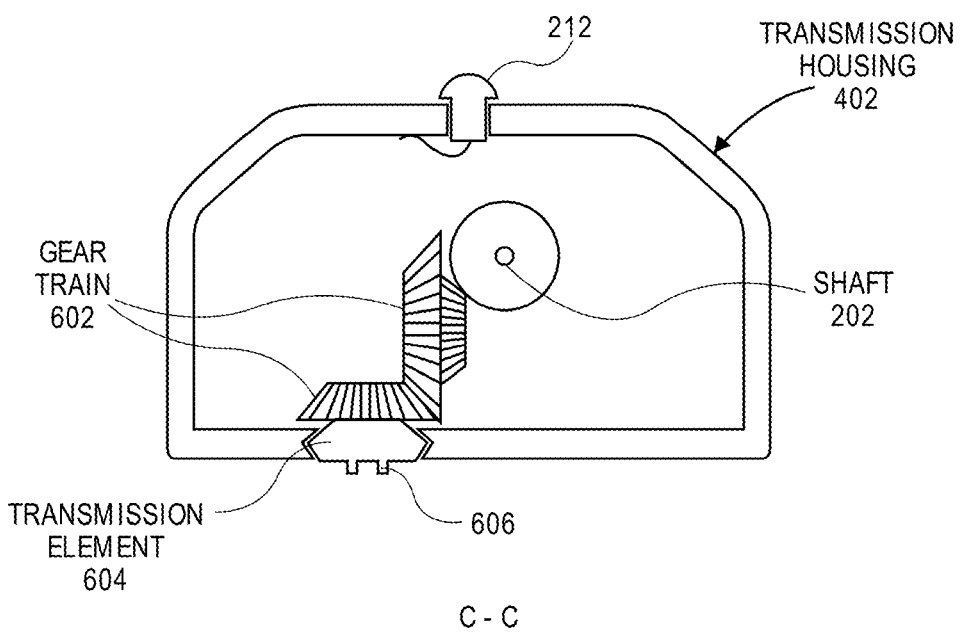
FIG. 6 is a cross-sectional view, taken about line C-C of FIG. 4, of a transmission housing of a surgical tool, in accordance with an embodiment.

Referring to FIG. 6, a cross-sectional view, taken about line C-C of FIG. 4, of a transmission housing of a surgical tool is shown in accordance with an embodiment. The endoscope can include a mechanical transmission to drive rotation of housing 208. The transmission can include transmission housing 402 and one or more mechanical transmission elements. By way of example, the endoscope may include a gear train 602 within transmission housing 402 to transmit power from an external source, e.g., a motor drive of robotic arm 112, to an output, e.g., housing 208. In an embodiment, transmission housing 402 includes a transmission element 604 coupled to housing 208 through one or more intermediate gears. Transmission element 604 can be a disc having input prongs 606 to engage with corresponding recesses in the motor drive of robotic arm 112. The motor drive can have a rotating output shaft, and rotation of the output shaft can be transmitted as torque to transmission element 604 through input prongs 606. Transmission element 604 may drive gear train 602. Gear train 602 can include several gears, e.g., spur or bevel gears, mounted on respective shafts within transmission housing 402. The mechanical transmission can also include belts and pulleys to transmit torque. The gears of gear train 602 may mesh to transmit torque from transmission element 604 to shaft 202 and/or housing 208. More particularly, shaft 202 may be connected to housing 208, and thus, when the transmission rotates one of shaft 202 or housing 208, the other of shaft 202 and housing 208 may also rotate.

In an embodiment, surgical tool 104 can incorporate a motor to rotate a tool component. For example, surgical tool 104 can be a surgical instrument, and a housing of surgical tool 104, e.g., housing 208 or transmission housing 402, can contain a motor to rotate a component of the surgical instrument. The motor can drive shaft 202 directly, e.g., shaft 202 may be connected to an output of the motor, or the motor can drive shaft 202 through gear train 602. Accordingly, the motor of surgical tool 104 can drive a camera, jaws, etc. of the surgical instrument.

Housing(s) of surgical tool 104 optionally contain processor 302 and/or other circuitry. For example, the housing(s) can contain an electrical circuit to provide power to tool components. The electrical circuit can deliver power to processor 302 or the motor described above. Similarly, the electrical circuit can deliver power to a component of the surgical instrument, such as a light emitting element, a cauterizer, etc. It will be appreciated, however, that processor 302 and other circuitry may be located in other components of surgical robotic system 100, e.g., user console 120 or control tower 130, and placed in communication with system components via wired or wireless connections.

Figure 7:
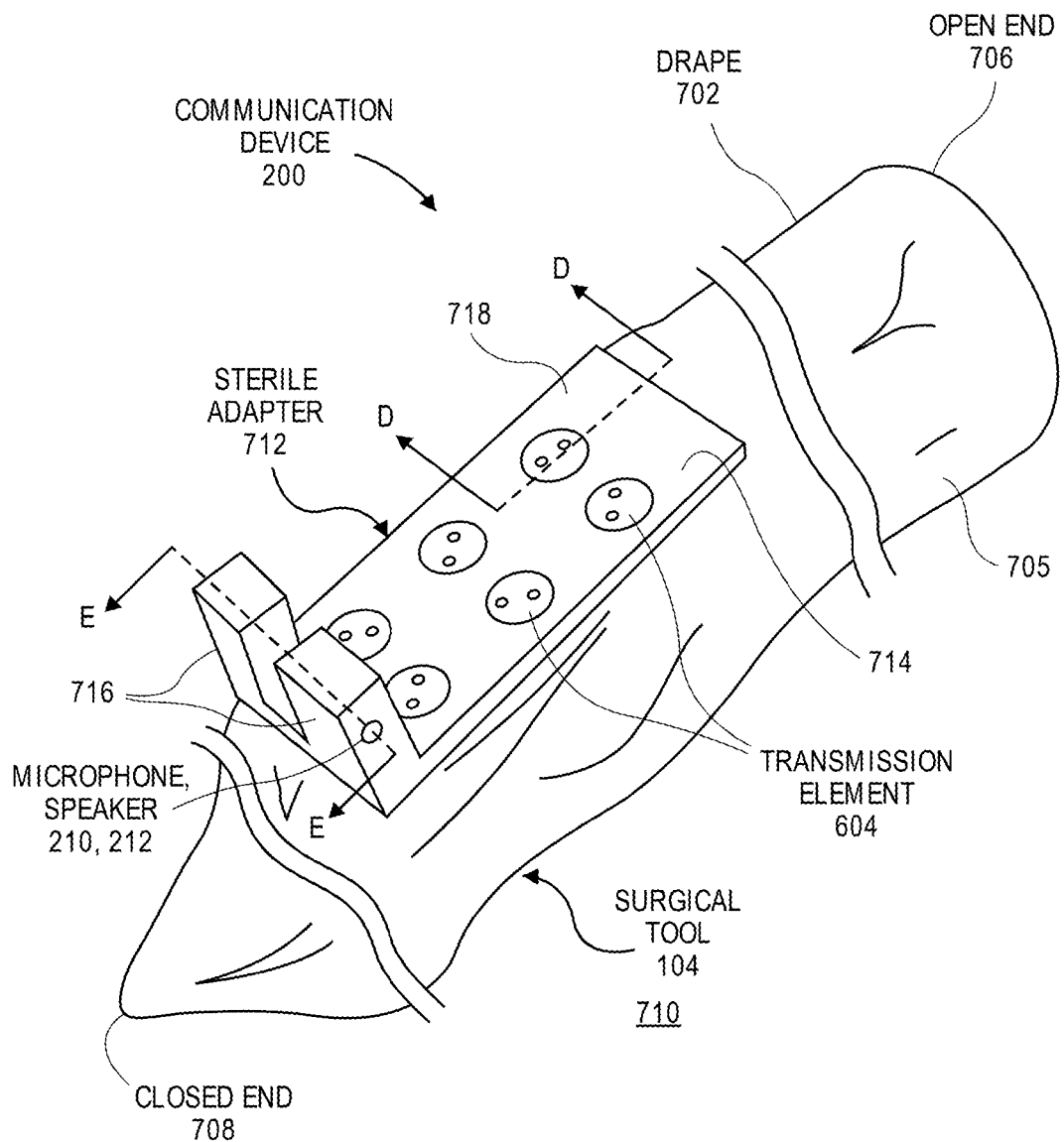
FIG. 7 is a perspective view of a communication device, in accordance with an embodiment.

Referring to FIG. 7, a perspective view of a communication device is shown in accordance with an embodiment. In an embodiment, surgical tool 104 of communication device 200 is a sterile barrier used to separate patient 102 and/or a component of surgical robotic system 100 from the surrounding environment. For example, surgical tool 104 may be sterile barrier having a drape that is placed over patient 102 during a surgery. The drape can be a woven fabric meeting the standard of practice related to surgical drapes. Similarly, the drape can be a polymer material meeting sterility requirements of the surgical procedure. By way of example, the drape can have a sheet-like or blanket-like shape to cover patient 102 on operating table 111.

The sterile barrier may include a drape 702 to be placed over robotic arm 112 of surgical robotic system 100. In an embodiment, drape 702 is a tubular sleeve that may be mounted over an end effector or some portion of a length of robotic arm 112. More particularly, the tubular sleeve can have a hollow cavity surrounded by a sleeve wall 705 to receive robotic arm 112. The hollow cavity may extend longitudinally through the tubular sleeve from an open end 706 to a closed end 708. Open end 706 and closed end 708 of the tubular sleeve may be defined by communication of an interior space of sleeve through the ends. More particularly, sleeve wall 705 may be between an interior space (hidden) of the sterile barrier and an exterior space 710, e.g., the surrounding environment. The interior space may be in fluid communication with exterior space 710 through open end 706 at a first longitudinal end of the tubular sleeve. By contrast, closed end 708 may separate the interior space from exterior space 710 at a second longitudinal end of the tubular sleeve. Accordingly, an end effector of robotic arm 112 may be disposed within the tubular sleeve near closed end 708 such that drape 702 covers a portion of robotic arm 112.

Surgical tool 104 can be coupled to robotic arm 112 around operating table 111 of surgical robotic system 100. For example, sterile adapter 712 may be operatively coupled to robotic arm 112 of surgical robotic system 100. An output shaft of a motor drive of robotic arm 112 may communicate with exterior space 710 through sterile adapter 712 incorporated in the sterile barrier. In an embodiment, drape 702 includes a cavity in sleeve wall 705 (FIG. 8) and sterile adapter 712 is integrated in the cavity. For example, sterile adapter 712 can be mounted on drape 702 over the cavity. Sterile adapter 712 can include one or more transmission elements 604 that engage with a motor drive of robotic arm 112 and a corresponding transmission element 604 (FIG. 6) of transmission housing 402 of the endoscope to allow the motor drive to drive rotation of housing 208 as described above. The endoscope can be mounted on a mounting body 714 of sterile adapter 712, e.g., by holding shaft 202 of the endoscope between a pair of prongs extending orthogonal to a mounting surface 718 of mounting body 714.

Sterile adapter 712 may include an audio transducer to facilitate communication between remote operator 107 and tableside staff 106. More particularly, one or more microphones may be mounted on an outer surface of sterile adapter 712. For example, microphone 210 may be mounted on sterile adapter 712 facing the surrounding environment to receive sound input 304 from tableside staff 106 and to convert the sound output into an audio signal, e.g., a microphone output signal, for transmission to user console 120. Similarly, speaker 212 may be mounted on sterile adapter 712 facing the surrounding environment to convert an acoustic output signal from processor 302 into a sound output to be heard by tableside staff 106. Furthermore, sterile adapter 712 may maintain a sterile barrier within the surgical arena. For example, sterile adapter 712 may cover the cavity in drape 702 to maintain exterior space 710 as the sterile zone and an interior space as a potentially non-sterile space.

All portions of the sterile barrier, including drape 702 and sterile adapter 712, may be sterilizable and disposable, whether drape 702 has a sheet-like or a tubular sleeve configuration. For example, drape 702 may be sterilizable by ethylene oxide or gamma sterilization processes.

Figure 8:
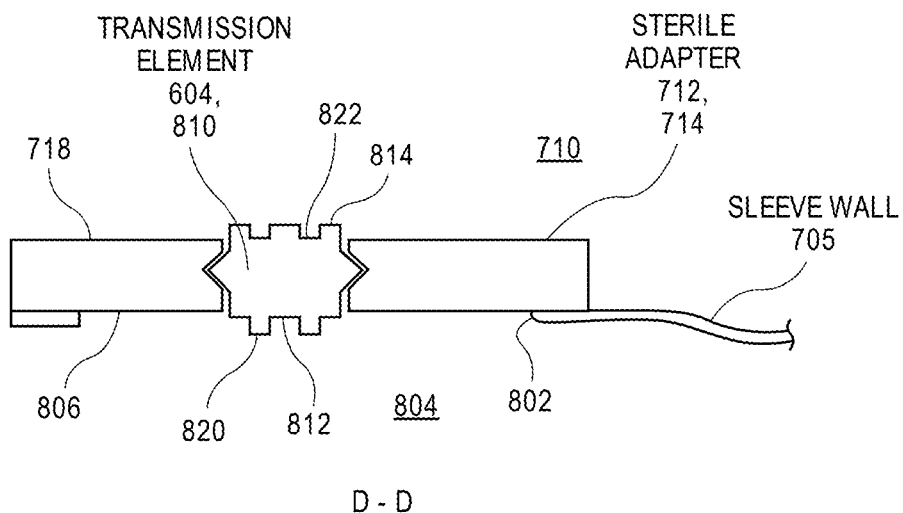
FIG. 8 is a cross-sectional view, taken about line D-D of FIG. 7, of a sterile adapter on a drape, in accordance with an embodiment.

Referring to FIG. 8, a cross-sectional view, taken about line D-D of FIG. 7, of a sterile adapter on a drape is shown in accordance with an embodiment. Drape 702 may be connected to a portion of sterile adapter 712. In an embodiment, drape 702 is attached to mounting body 714 of sterile adapter 712 around a cavity 802. For example, cavity 802 may be in sleeve wall 705, extending from exterior space 710 into an interior space 804, and sterile adapter 712 can be mounted on sleeve wall 705 over cavity 802. Sleeve wall 705 can be attached to sterile adapter 712 using adhesive or thermal welding techniques. For example, when drape 702 is a sheet-like fabric surgical drape, sterile adapter 712 may be attached to drape 702 by an adhesive seal, such as a seal formed by a silicone adhesive sealant. Alternatively, when drape 702 is a polymeric tubular sleeve, sterile adapter 712 may be attached to drape 702 by an adhesive seal, such as a seal formed by a cyanoacrylate bond, or by a thermal weld, such as an ultrasonically formed thermal joint. Mounting body 714 may be attached to sleeve wall 705 around cavity 802 such that an inner surface 806 of sterile adapter 712 faces interior space 804. Similarly, an outer surface, such as mounting surface 718, may face exterior space 710. In an embodiment, the outer surface is positioned above drape 702, and accordingly, microphone 210 or speaker 212 can be mounted above drape 702 facing exterior space 710.

In an embodiment, sterile adapter 712 includes transmission element 604 extending through mounting body 714 from interior space 804 to exterior space 710. Transmission element 604 may extend through sterile adapter 712 from a region between the sterile barrier and operating table 111 to a region within the surrounding environment. Transmission element 604 may include a drive disc 810 having an input face 812 exposed to interior space 804 and an output face 814 exposed to exterior space 710. Accordingly, input face 812 may be within a nonsterile interior space 804 defined by sterile adapter 712, and output face 814 may be within a sterile exterior space 710 defined by sterile adapter 712. Drive disc 810 may be retained within mounting body 714 by snap detents formed around a disc sidewall that engages a corresponding channel formed in a sidewall of a hole extending through mounting body 714.

Input face 812 or output face 814 may be parallel to each other. The faces may include features to engage with corresponding driving or driven mechanisms. More particularly, drive disc 810 may include a boss 820 extending into interior space 804 from input face 812. Boss 820 may be sized and configured to engage with a corresponding recess in an end effector of robotic arm 112. More particularly, the end effector may be an output shaft of a motor drive to transmit torque to drive disc 810 via boss 820. Drive disc 810 may include a recess 822 extending into output face 814 from exterior space 710. Recess 822 may be sized and configured to receive a corresponding protrusion on a surface of the endoscope, e.g., input prong 606, when the endoscope is attached to mounting surface 718 of sterile adapter 712. Accordingly, torque input to boss 820 by a motor drive may be transmitted to recess 822 and to input prong 606 inserted into recess 822 when the endoscope and sterile adapter 712 are joined in surgical robotic system 100. Boss 820 and recess 822 are provided by way of example and not limitation. That is, input face 812 and output face 814 may include bosses, recesses, or other features that can engage a mating surface, e.g., as a keyed attachment.

Figure 9:
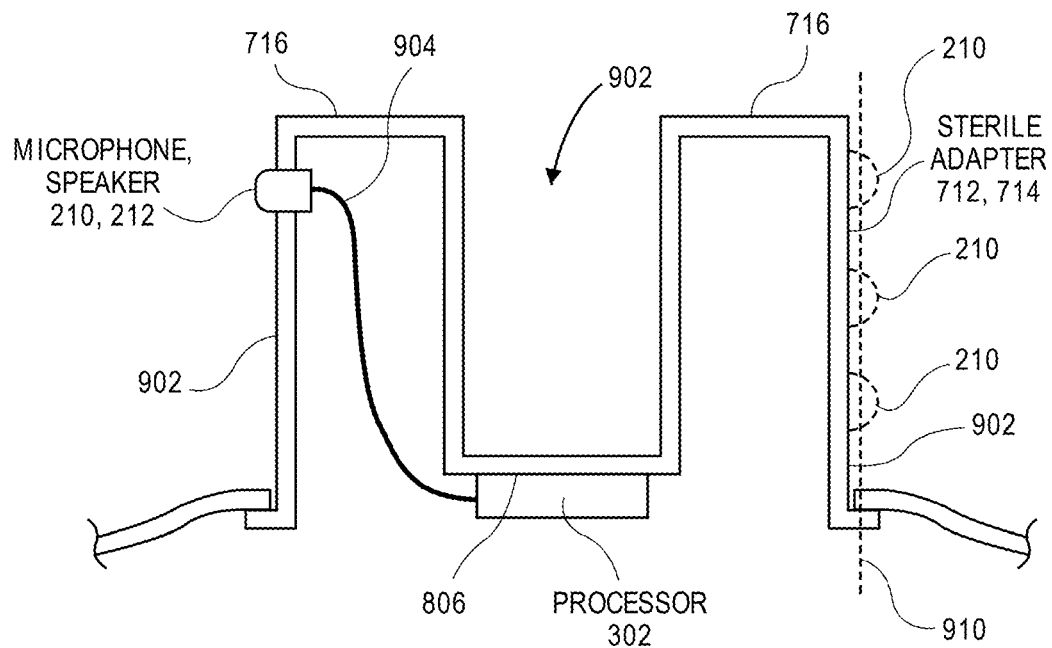
FIG. 9 is a cross-sectional view, taken about line E-E of FIG. 7, of a sterile adapter on a drape, in accordance with an embodiment.

Referring to FIG. 9, a cross-sectional view, taken about line E-E of FIG. 7, of a sterile adapter on a drape is shown in accordance with an embodiment. Electronics may be mounted on sterile adapter 712. In an embodiment, an audio transducer is mounted on sterile adapter 712. For example, microphone 210 and/or speaker 212 may be located on a sidewall 902 of mounting body 714 facing toward the surrounding environment. In an embodiment, microphone 210 and/or speaker 212 are integrated within a rigid plastic portion of mounting body 714. For example, mounting body 714 may be molded around microphone 210. Microphone 210 may be located on an outward facing surface of holding prong 716 such that a front volume of microphone 210 faces the surrounding environment. Accordingly, microphone 210 may receive sound input 304 propagating toward sterile adapter 712 from the surrounding environment. Other circuitry mounted on sterile adapter 712 can include light sources, such as light emitting diodes, to indicate a status of microphone 210 or speaker 212 to a user, e.g., whether a microphone or a speaker is muted.

In an embodiment, several microphones 210 (shown in phantom) may be mounted on outer surface 209. The several microphones 210 can be positioned with a predetermined relative spacing to facilitate audio processing of respective microphone output signals in a manner similar to the methods described above. For example, two or more, e.g., three, microphones 210 can be positioned equidistantly with each other on outer surface 209 to form a line 910 extending through the microphones. A spacing of microphones 210 along line 910 can allow processor 302 to perform time of arrival processing of microphone output signal to detect a source location of a sound input and/or to measure and reduce background noise in the audio signals, as described above. It is noted that microphones 210 may be located on any region of outer surface 902, and thus, may form line 210 extending in different directions other than the vertical direction that is illustrated.

An inward facing surface of holding prong 716 may face a counterpart inward facing surface of an adjacent holding prong 716 across a holding channel 902. Holding channel 902 may be located between adjacent holding prongs 716 to receive a portion of the endoscope, e.g., shaft 202. Holding prongs 716 may extend upward on opposite lateral sides of shaft 202 to constrain lateral movement of shaft 202 when the endoscope is mounted on mounting surface 718 of sterile adapter 712.

Surgical tool 104 can include an interface mounted on sterile adapter 712 to couple the one or more microphone(s) 210 electrically and communicatively to another component of surgical robotic system 100. For example, an electrical connector 904 may be electrically connected to microphone 210, and electrical connector 904 may extend to processor 302 and/or robotic arm 112. Electrical connector 904 can pass through mounting body 714 from outer surface 209, e.g., sidewall 902, to inner surface 806. For example, electrical connector 904 may be an electrical pin passing through a plastic wall of mounting body 714 to connect to an electrical terminal of an audio transducer, e.g., microphone 210. Electrical connector 904 may include a connector affixed to mounting body 714 and connected to a mating connector, e.g., by an electrical wire. More particularly, electrical connector 904 may include an electrical wire, an electrical cable, or an electrical trace extending through the interior space 804 and/or over inner surface 806 of mounting body 714 from a first connector to a second connector. The first connector may be electrically connected to microphone 210 and the second connector may be electrically connected to processor 302. Electrical connector 904 may electrically connect microphone 210 to processor 302 such that processor 302 is communicatively coupled to microphone(s) 210 to process and transmit audio signals generated by microphone(s) 210. Similarly, a housing of the audio transducer may extend through a wall of sterile adapter 712, and thus, electrical connector 904 may be connected to microphone 210 or speaker 212 within interior space 804. Electrical connector 904 may extend from microphone 210 or speaker 212 to processor 302 to transmit acoustic electrical signals through interior space 804 to or from processor 302. More particularly, the processor 302 may be mounted on inner surface 806 of mounting body 714, and electrical connector 904 may extend from microphone 210 or speaker 212 to processor 302. As such, processor 302 can be electrically connected to microphone 210 or speaker 212 by electrical connector, and processor 302 may exchange acoustic electrical signals with microphone 210 or speaker 212 through electrical connector 904. Processor 302, microphone 210, and/or speaker 212 may also receive power input signals from an external source. For example, microphone 210 or speaker 212 may receive power from robotic arm 112 via pin contacts between circuitry mounted on sterile adapter 712 and corresponding circuitry integrated in an end effector of robotic arm 112. Alternatively, power may be transferred from robotic arm 112 to processor 302, microphone 210, or speaker 212 using wireless power transfer, e.g., resonant inductive coupling, between circuitry mounted on sterile adapter 712 and corresponding circuitry integrated in an end effector of robotic arm 112.

The sterile barrier can include a sterile barrier sleeve as a component to cover each robotic arm used during any surgical robotic procedure. More particularly, surgical robotic system 100 may include several robotic arms 112 mounted at respective locations on operating table 111, and each robotic arm 112 may be covered by a tubular sleeve such that a motor drive of the robotic arm 112 engages a respective sterile adapter 712 to drive a respective surgical tool 104 (e.g., having an endoscope) mounted on the respective sterile adapter 712. By way of example, surgical robotic system 100 may include a first surgical tool 104, e.g., a first sterile barrier sleeve covering a first robotic arm 112, and having a first microphone 210, and a second surgical tool 104, e.g., a second sterile barrier sleeve covering a second robotic arm 112, and having a second microphone 210. The first microphone 210 may pick up sound input from a first tableside staff 106 on a first side of operating table 111, and the second microphone 210 may pick up sound input from a second tableside staff 106 on a second side of operating table 111. Furthermore, the first microphone 210 can convert the first sound input into a first microphone output signal and the second microphone 210 can convert the second sound input into a second microphone output signal.

In an embodiment, remote operator 107 may focus communication facilitated by surgical tools 104 to a specific location around operating table 111. User console 120 may be communicatively coupled to the first microphone 210 and the second microphone 210, e.g., through electrical cable 214. A location of the microphones 210 around operating table 111 may be known to user console 120 because a data channel used to pass the respective microphone output signals of each microphone 210 may be identifiable. That is, the data channel transferring the microphone output signal from surgical tool 104 to user console 120 may be known to correspond to a particular robotic arm 112 on operating table 111, e.g., at a patient left side or at a patient right side. Based on the known location of the corresponding robotic arm 112, remote operator 107 can select, using a console of user console 120, a particular location to communicate to. For example, remote operator 107 may use an input device of user console 120 to provide a command to a console processor (FIG. 10) to select one or more of the first microphone output signal of the first microphone 210 or the second microphone output signal of the second microphone 210 for output by console speaker 150.

The remote operator 107 may choose to communicate with a first tableside staff 106 on a patient left side using a speaker 212 mounted on a sterile barrier covering a first robotic arm 112 and a microphone 210 mounted on a first endoscope attached to a sterile adapter 712 of the sterile barrier. Similarly, the remote operator 107 may choose to communicate with a second tableside staff 106 on a patient right side using a speaker 212 mounted on a sterile barrier having a sleeve covering a second robotic arm 112 and a microphone 210 mounted on a second endoscope attached to a sterile adapter 712 of the sterile barrier. In other embodiments, both the microphone 210 and speaker 212 may be attached to the same surgical tool 104 selected by the remote operator 107. For example, both microphone 210 and speaker 212 on the endoscope or on the sterile barrier. Accordingly, the remote operator 107 can select a specific region of the operating arena to focus communications toward.

In addition to selecting a specific channel to focus communications to a region of the operating arena, the separate microphones 210 of surgical robotic system 100 may be used in combination to direct listening to the region. More particularly, the microphones 210 mounted on different robotic arms 112 of surgical robotic system 100 may form a microphone array that can be used for acoustic beam forming to enhance audio quality. As described above with respect to FIG. 3, the microphone array may generate several microphone output signals that may be processed to perform noise reduction or to detect sound direction. Processing may be performed by a console processor of computer system 110. For example, a first microphone 210 mounted on a first sterile barrier having a sleeve covering a first robotic arm 112 may act as primary microphone 210A and a second microphone 210 mounted on a second sterile barrier having a sleeve covering a second robotic arm 112 may act as a secondary microphone 210B. Microphone output signals from primary microphone 210A and secondary microphone 210B may be processed by the console processor using audio processing algorithms, e.g., noise reduction algorithms, time of arrival algorithms, or beam forming algorithms, to better capture a voice of tableside staff 106, to reduce background noise, and to improve vocal communications between tableside staff 106 and surgeon 107.

Figure 10:
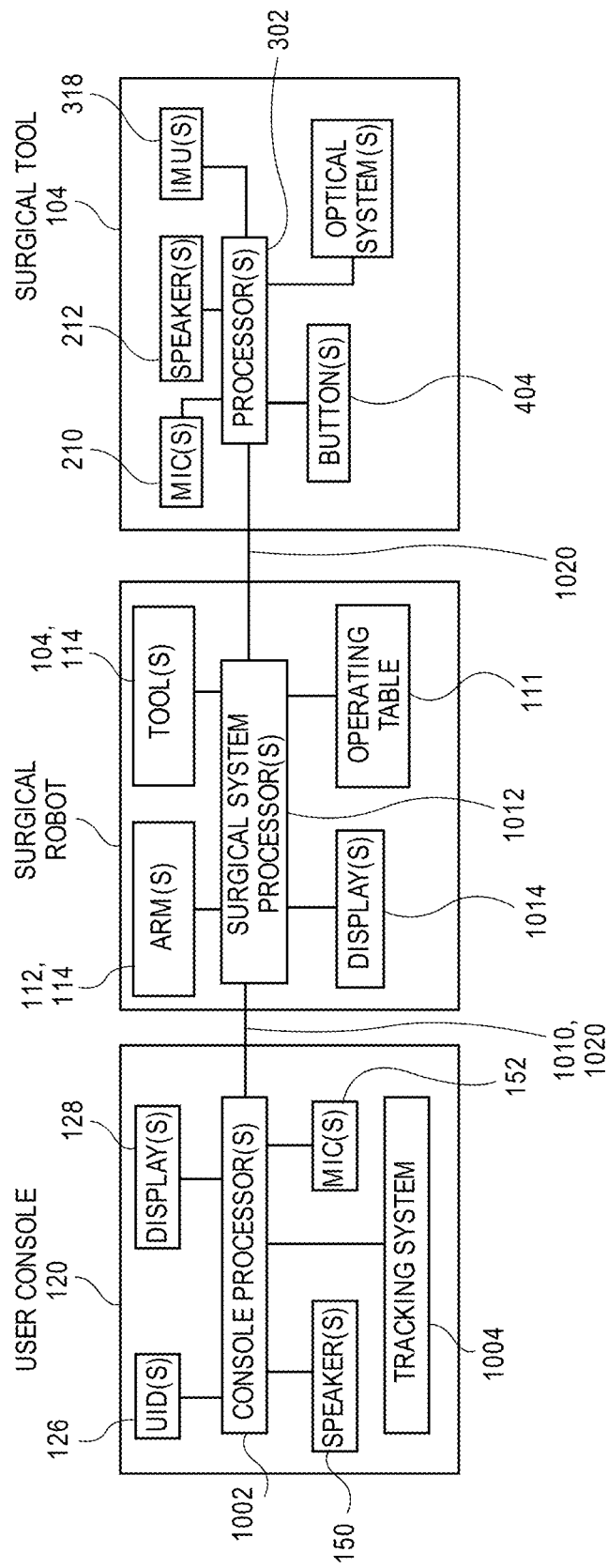
FIG. 10 is block diagram of a computer portion of a surgical robotic system, in accordance with an embodiment.

Referring to FIG. 10, a block diagram of a computer portion of a surgical robotic system is shown in accordance with an embodiment. Surgical robotic system 100 can include: user console 120 having computer system 110, a surgical robot having robotic components such as arms 112, surgical tool(s) 104, and optionally corresponding actuators 114. User console 120 may be in electrical communication with surgical tool 104 of communication device 200. The surgical robotic system has circuitry suited to specific functionality, and thus, the diagrammed circuitry is provided by way of example and not limitation.

Console processor(s) 1002 may receive electrical input signals from surgical tool 104 or from other components of user console 120. For example, console processor 1002 can receive microphone output signals from console microphone(s) 152. Console processor 1002 can receive operator command signals from a touchscreen menu button, a keyboard, a pointing device, or another user input device that is manipulated by remote operator 107, such as foot pedals 124. Console processor(s) 1002 may output signals to other components of user console 120. For example, console processor 1002 can output acoustic output signals to console speaker(s) 150. Console processor 1002 can output video data for display to remote operator 107 on a display device 128. One or more seat actuators can receive control signals from console processor 1002 to control movement of seat 122. Console processor 1002 can process input signals to determine and provide output signals. For example, microphone output signals from console microphone 152 may be processed to generate acoustic output signals for transmission to surgical tool 104.

Console processor(s) 1002 of user console 120 can control portions of the surgical robot, e.g., robotic arms 112 and/or surgical tools 104. UID 126 may be communicatively coupled to console processor 1002 and/or a surgical robotic system processor 1012 of surgical robotic system 100 to provide input commands to control surgical robotic system 100. For example, UID 126 may communicate electrical control signals to computer system 110, e.g., spatial state signals generated by a UID processor in response to signals from a tracking sensor of a tracking system 1004. The electrical signals may be input commands to cause motion of surgical robotic system 100.

Console processor(s) 1002 of computer system 110, surgical systems processor(s) 1012, or processor(s) 302 may execute instructions to carry out the different functions and capabilities described above. The instructions executed by the processor(s) may be retrieved from a local memory, which may include a non-transitory machine-readable medium. The instructions may be in the form of an operating system program having device drivers to control components of surgical robotic system 100, e.g., arm or tool actuators 114 operatively coupled to robotic arm(s) 112 or surgical tool(s) 104. The instructions stored on the non-transitory machine-readable medium can be executed by the processor(s) to cause surgical robotic system 100 to perform any of the methods or operations described herein.

Console processor 1002 can output control signals 1010 to surgical system processor(s) 1012 via a wired or wireless link. Control signals 1010 may be transmitted to control movement of the surgical robot. For example, at least one processor 1012 can be located in control tower 130, and may be communicatively coupled to system components, such as arm(s) 112, operating table 111, or one or more displays 1014.

Actuators 114 of surgical robotic system 100 may receive control commands from surgical system processor 1012 to cause motion corresponding to movement of UID 126. For example, an input command received by UID 126, such as a tilting hand motion, can result in a control command to move an arm actuator 114 and thereby an end effector mounted on arm 112.

Surgical tool 104 may include one or more processor 302 to execute instructions to carry out the different functions and capabilities described above. Instructions executed by processor(s) 302 of surgical tool 104 may be retrieved from a local memory. Processor 302 of surgical tool 104 may include a field-programmable gate array configured to perform specific functions, such as digital signal processing for audio processing functionality. Processor(s) 302 may receive input signals from console processor 1002, e.g., directly or via surgical system processor 1012. Processor(s) 302 may receive input signals from other components of surgical tool 104. For example, processor 302 can receive audio signals from console processor 1002 that correspond to speech of operator 107 and intended for playback to operator 106. Processor 302 can receive microphone output signals from microphone(s) 210 that correspond to speech of operator 106 that is intended for communication to console processor 1002 and playback to operator 107. Processor 302 can receive orientation signals from IMU 318, processor 302 can receive image data signals from the optical subsystem, or processor 302 can receive operator command signals from buttons 404 that are manipulated by tableside staff 106. The input and output signals of processor(s) 302 provide for the functionality described above. For example, processor(s) 302 may output acoustic output signals to speaker(s) 212 to communicate to operator 106, or processor 302 can output illumination signals to the optical subsystem to facilitate imaging within patient 102. Computer components of the surgical robotic system 100 may communicate with surgical tool 104. For example, the computer components and the tool can communicate data and/or power signals to each other via wired or wireless communication links 1020. Communication link 1020 may include a wired connection via electrical cable 214. Electrical cable 214 may include an audio jack or other wired connectors to transfer data or power electrical signals between surgical tool 104 and control tower 130 or user console 120. Furthermore, in an embodiment, surgical tool 104 communicates wirelessly with user console 120 or control tower 130. More particularly, a wireless communication link 1020 may be established by respective RF circuitry of the computer components and surgical tool 104. The system processors can process respective audio signals to facilitate two-way communication between remote operator 107 at user console 120 and tableside staff 106 at surgical tool 104.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A medical device, comprising:
   a drape having an exterior surface facing an exterior space, wherein the drape is pliable;
   one or more microphones mounted on and over the exterior surface of the drape such that the one or more microphones are exposed to the exterior space, wherein the one or more microphones are configured to receive a sound input and convert the sound input into one or more microphone output signals; and
   a processor communicatively coupled to the one or more microphones to process the one or more microphone output signals.

2. The medical device of claim 1, wherein the one or more microphones are integrated with the drape.

3. The medical device of claim 1, wherein the drape includes one or more of a woven fabric or a polymeric film.

4. The medical device of claim 1, wherein the drape includes a drape wall surrounding a cavity to receive a robotic arm.

5. The medical device of claim 1, wherein the drape is tubular shaped, and includes an open end and a closed end.

6. The medical device of claim 1 further comprising one or more speakers exposed to the exterior space, wherein the one or more speakers are above the drape.

7. The medical device of claim 1, wherein processing the one or more microphone output signals includes detecting a source location of the sound input based on a time difference of arrival at the one or more microphones.

8. The medical device of claim 1, wherein processing the one or more microphone output signals includes measuring a background noise and reducing the background noise.

9. The medical device of claim 1 further comprising a sterile adapter coupled to the drape, wherein the sterile adapter includes one or more transmission elements to engage a motor drive of a robotic arm.

10. The medical device of claim 9 further comprising an interface mounted on the sterile adapter to couple the one or more microphones electrically and communicatively to one or more of the robotic arm or the processor.

11. A surgical system, comprising:
    a surgical instrument; and
    a medical device including a drape covering the surgical instrument and having an exterior surface facing an exterior space, wherein the drape is pliable, one or more microphones mounted on and over the exterior surface of the drape such that the one or more microphones are exposed to the exterior space, wherein the one or more microphones are configured to receive a sound input and convert the sound input into one or more microphone output signals, and a processor communicatively coupled to the one or more microphones to process the one or more microphone output signals.

12. The surgical system of claim 11, wherein the drape includes a drape wall surrounding a cavity to receive the surgical instrument.

13. The surgical system of claim 11 further comprising one or more speakers exposed to the exterior space, wherein the one or more speakers are above the drape.

14. The surgical system of claim 11, wherein processing the one or more microphone output signals includes detecting a source location of the sound input based on a time difference of arrival at the one or more microphones.

15. The surgical system of claim 11, wherein processing the one or more microphone output signals includes measuring a background noise and reducing the background noise.

16. The surgical system of claim 11 further comprising a sterile adapter coupled to the drape, wherein the sterile adapter includes one or more transmission elements to engage a motor drive of the surgical instrument.

17. The surgical system of claim 16 further comprising an interface mounted on the sterile adapter to couple the one or more microphones electrically and communicatively to one or more of the surgical instrument or the processor.

18. A surgical robotic system, comprising:
    a first medical device including a first drape covering a first robotic arm, wherein the first drape is pliable, and a first microphone mounted on and over a first exterior surface of the first drape, wherein the first microphone is configured to receive a sound input and convert the sound input into a first microphone output signal;
    a second medical device including a second drape covering a second robotic arm, wherein the second drape is pliable, and a second microphone mounted on and over a second exterior surface of the second drape, wherein the second microphone is configured to receive the sound input and convert the sound input into a second microphone output signal; and
    a processor communicatively coupled to the first microphone and the second microphone to process the first microphone output signal and the second microphone output signal.

19. The surgical robotic system of claim 18, wherein processing the first microphone output signal and the second microphone output signal includes detecting a source location of the sound input based on a time difference of arrival at the first microphone and the second microphone.

20. The surgical robotic system of claim 18, wherein processing the first microphone output signal and the second microphone output signal includes measuring a background noise and reducing the background noise.

\* \* \* \* \*